United States Patent [19]

Lather et al.

[11] 4,162,636
[45] Jul. 31, 1979

[54] MOUNT FOR ULTRASONIC TEST HEAD

[75] Inventors: Dieter Lather, Rheurdt; Wolfgang Terschüren, Mülheim; Kurt Hannoschöck, Sonsbeck II; Günter Simoneit; Karl Ries, both of Mülheim, all of Fed. Rep. of Germany

[73] Assignee: Mannesmann Aktiengesellschaft, Dusseldorf, Fed. Rep. of Germany

[21] Appl. No.: 856,223

[22] Filed: Dec. 1, 1977

[30] Foreign Application Priority Data
Dec. 3, 1976 [DE] Fed. Rep. of Germany ....... 2655364

[51] Int. Cl.² ............................................ G01N 29/04
[52] U.S. Cl. .................................................. 73/638
[58] Field of Search ............... 73/620, 622, 629, 633, 73/634, 635, 637, 638, 644

[56] References Cited

U.S. PATENT DOCUMENTS

| | | | |
|---|---|---|---|
| 3,628,375 | 12/1971 | Pagano | 73/644 X |
| 3,752,255 | 8/1973 | Hill et al. | 73/633 X |
| 3,952,581 | 4/1976 | Gottelt | 73/641 X |
| 3,952,582 | 4/1976 | Graham et al. | 73/644 X |

FOREIGN PATENT DOCUMENTS 139138  6/1960  U.S.S.R. ..................... 73/644

Primary Examiner—Anthony V. Ciarlante
Attorney, Agent, or Firm—Smyth, Pavitt, Siegemund, Jones & Martella

[57] ABSTRACT

An ultrasonic transducer is held in a tubular holder which in turn is axially placed in a mount. A frame depends from a cover of a gimbal mounted container for coupler fluid and the mount is clamped to the frame at an adjustable angle so that the transducer axis always intersects the same point. Ball rollers on the cover position the container in relation to a pipe to be tested so that said point is located on the pipe's surface. The transducer holder has a shoulder onto which one may seat a calibration standard.

5 Claims, 4 Drawing Figures (A-A)

MOUNT FOR ULTRASONIC TEST HEAD

BACKGROUND OF THE INVENTION

The present invention relates to mounting a testhead in a device for ultrasonic testing of welding seams of large pipes. The welding seam may, for example, have resulted from submerged arc welding.

In a copending application of some of us, Ser. No. 767,353 filed Feb. 10, 1977, an apparatus is disclosed which is constructed for ultrasonic inspection of pipes. This apparatus includes particularly constructed holders for gimbal mounted water tanks which are to be placed into particular positions in relation to the pipe to be inspected, the positions having particular relation to the welding seam of that pipe to be inspected as to defects. The water tanks each contain coupler fluid in which the testhead is immersed. The testhead is or includes an ultrasonic transducer. The present invention relates particularly to a new and improved device for mounting the testhead (transducer) in this water tank and for establishing a definite orientation to the tank as such.

DESCRIPTION OF THE INVENTION

It is an object of the invention to provide a new and improved mounting structure for ultrasonic transducers in a container for coupler fluid, which permits establishing a positive and reproducible orientation of the transducer as mounted, whereby particularly a calibration standard can be affixed to the mounted head in such a manner that a definite relation is established between the standard and the head, so that test results and calibration data can be correlated in a reproducible fashion.

In accordance with the preferred embodiment of the present invention, it is suggested to provide the container with an open top on which is placed a cover plate, and a frame, preferably two plates, extended down from the plate, into the container, for mounting a mount, preferably being of tubular construction and having an axis which can be differently oriented on account of orienting the mount differently in the frame and clamping it thereto. The transducer is mounted in the mount preferably coaxially therewith and is oriented thereby. The transducer is preferably of tubular construction and inserted in a tubular holder which in turn is inserted in the mount in coaxial relation thereto. The holder is preferably provided with a shoulder onto which one may place a calibration standard. The frame plates are preferably provided with arcuate slots, and the mount is clamped to the edges of these slots, resulting in the selected orientation thereof. The slots are configured so that the axis of the mounted transducer traverses always a particular center point. The cover plate is provided with means for positioning the container with inserted testhead in relation to the surface of the object (pipe) to be tested, so that that center point coincides with the entrance point for ultrasonic waves launched by the transducer.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

Proceeding now to the detailed description of the drawings, FIG. 1 shows a frame 2 which, in the general sense, is a part of a test stand for ultrasonic equipment. More particularly, frame 2 may be a portion of a cardan or gimbal mount for a case, container or water tank 5 (see cardan mount 15 in said application Ser. No. 767,353). Pins 1 provide for pivoting of case or container 5 about a first gimbal axis that runs horizontally and in the plane of the drawing (or parallelly thereto) of FIG. 1. Pins 1' in FIG. 2 refer to a set of pivot pins being aligned with and defining a second gimbal axis which extends transversely to the axis of pins 1.

Figure 1:
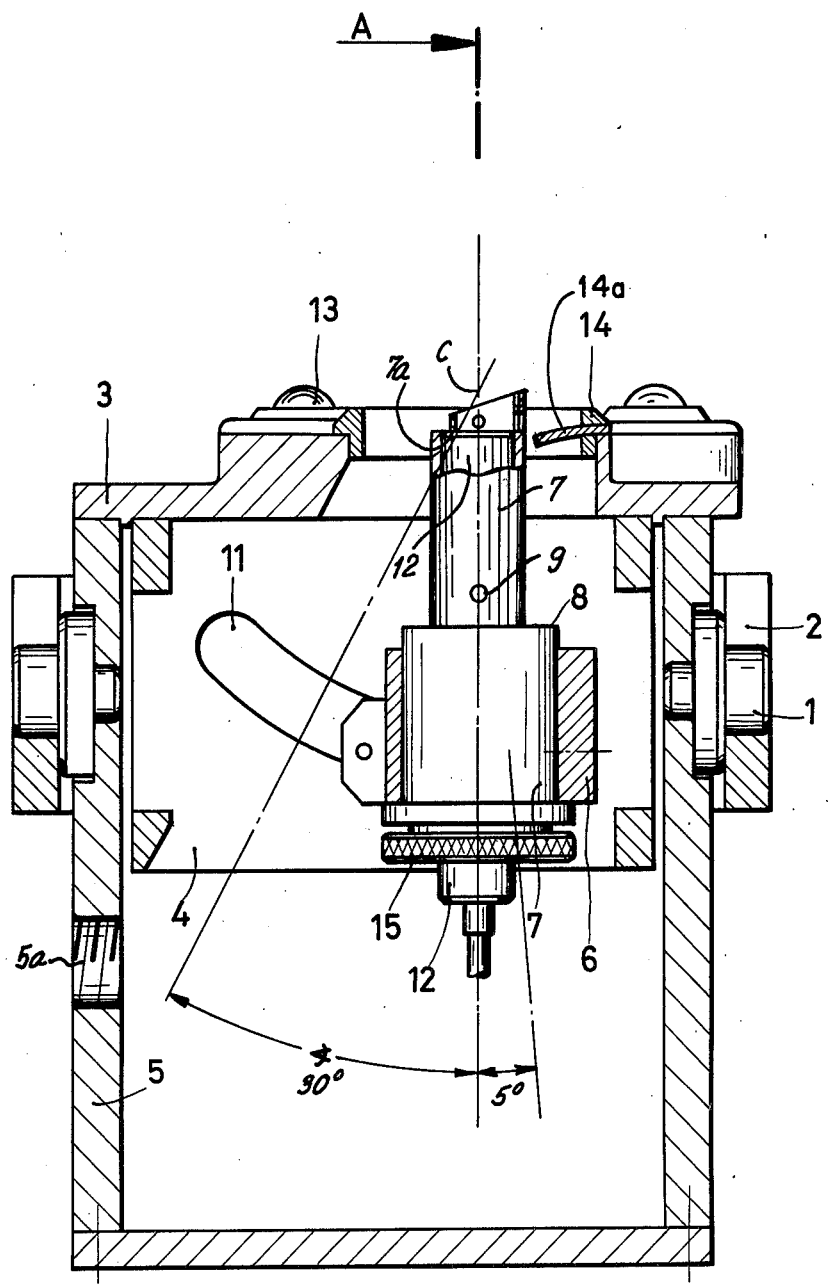
FIG. 1 is a cross-section through the transducer mount in accordance with the present invention.
Figure 2:
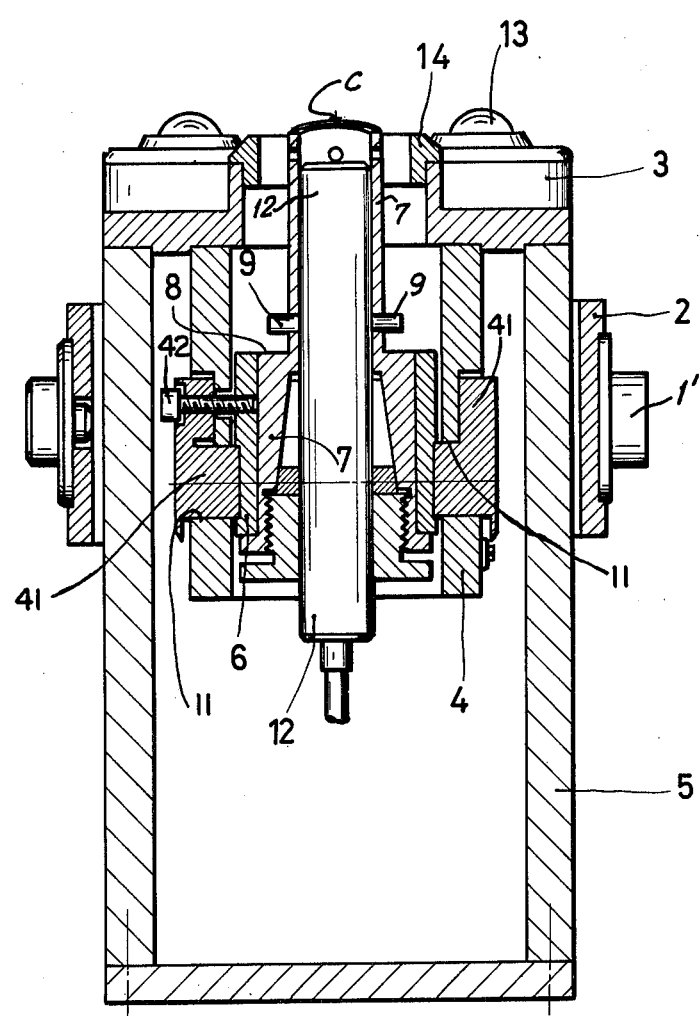
FIG. 2 is a section view taken along lines A—A in FIG. 1.

The container 5 is open at the top and carries a cover plate 3 from which extends a frame 4 which occupies about the upper half of container 5. Frame 4 supports a mounting piece, sleeve or mount 6 which is clamped or otherwise secured to frame 4. The frame 4 is basically comprised of two downwardly extending plates having two aligned arcuate slots such as 11 to establish different angular positions of the mount 6 and defining particularly the orientation of the center axis of a cylindrical or tubular opening of the mount 6. Mounting and positioning pieces 41 for the mount 6 are received in the slots 11, a bolt such as 42 clamps one of the pieces 41 to one of the plates 41. The character c denotes the center about which the axis of mount 6 appears to be turned in the different mounting positions along arcuate slots 11. The mount 6 receives the test head which is comprised of an ultrasonic transducer 12, operable, for example, as transmitter and as receiver. The transducer 12 is basically of cylindrical construction and is mounted in a test head sleeve 7 having a lower, socket like, large diameter portion and a narrow upper part, there being an annular shoulder 8 accordingly. The test head transducer 12 sits in a cap screw 15 which is threaded into the socket portion of transducer holder 7. The transducer 12 will be inserted into the holder 7 until the front end of transducer 12 abuts a stop 7a in the front portion of holder 7. This orients and positions the transducer in the holder 7. Moreover, holder 7 is of tubular construction and when inserted in mount 6, it establishes a coaxial relation therewith. Moreover, the transducer 12 has an axis along which and in which it launches ultrasonic waves, and this axis will coincide with the axes of mount 6 at holder 7, so that the inserted transducer is in fact placed on the axis which is positioned and oriented by the frame mount. The transducer axis will, therefore, always traverse point c.

The top of cover 13 is provided with altogether four (or more) ball rollers 13 which are provided to engage the surface of the object (pipe) which is subjected to the ultrasonic transducing. The ball rollers 13 have such an orientation (possibly an adjustable one) so that upon engaging the curved surface of a pipe to be inspected ultrasonically, the point c will always be located on that surface. This then becomes the point through which ultrasonic vibrations enter the pipe after having been launched by the transducer.

Cover 3 has an opening defined and lined by insert 14, through which projects the front end (bevelled cut) of transducer holder 7. This insert 14 is provided with a plastic tongue 14a which prevents parasitic ultrasonic waves from being directed out of the cavity of container 5 towards the test object. These waves may have resulted from parasitic waves emitted by transducer 12 into the container 5 in directions other than along the desired axial direction, and after reflections by the container walls these waves may be directed out of the opening of insert 14; tongue 14a prevents such interference and noise generation.

Figure 4:
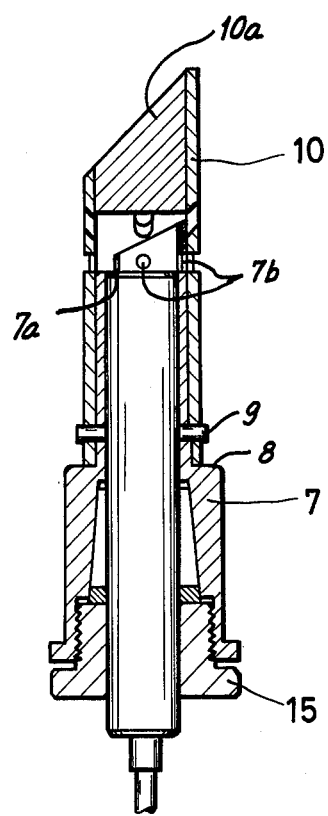
FIG. 4 is a section view through the assembly shown in FIG. 3.
Figure 3:
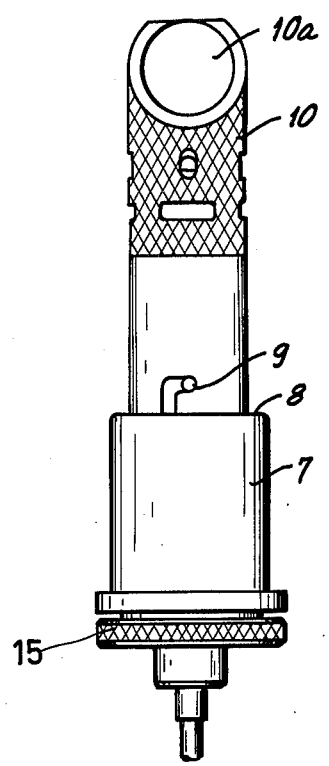
FIG. 3 is a front view of a testhead with a calibration standard connected thereto.

The FIGS. 3 and 4 show, additionally, a device 10, which should be disregarded for the moment. For purposes of assembly, the frame 4 on plate 3 is removed from the container 5, and the holder 6 is oriented in the desired direction and fixed, i.e. clamped to plates 4. The arcuate slot may for example permit an adjustment from 30° to one side, to 5° to the other side. It can readily be seen from FIG. 1 that the pivot point c for this adjutment will be located a little above the opening in cover 3. After the holder 7 with inserted transducer 12 has been affixed and positioned in frame 4, cover 3 is screwed (e.g. bolted) to the top of container 5. Since the front end of transducer 12 abuts the stop 7a in holder 7, the transducer's position is now well defined in relation to the cardanically (gimbal) mounted container 5.

The cardan mount is completed by connecting the pins 1' to a fork of the type shown in FIG. 3 in the above identified application Ser. No. 767,353. Quick release couplings will be used to complete the electrical connections to the transducer. Reference numeral 5a refers to a water connection for charging the container 5 with pressurized water which emerges from and through insert 14 and forms a water cushion between transducer 12 and the object to be tested which engages the rolls 13. Openings 7b in holder 7 ensure the presence of water right at the front end of the transducer 12. This way a water coupling path is established between the transducer 12 and the test object, such as a large pipe. These conditions are maintained regardless of the angular orientation of the assembly 6,7,12. Moreover, the entrance point of acoustic waves into the test object, c, remains the same, so that the length of the coupler path from the transducer 12 to the test object remains also the same for different orientations.

Turning now to the device 10, this device constitutes a calibrator element explained in greater detail in co-pending application Ser. No. 822,919, filed 8-8-77. This calibration device, element or standard can be slipped over holder 7. The holder 7 has several pins 9, and tubular device 10 has a corresponding number of angle slots to establish a bayonette like connection. The disposition of the standard 10 is established in relation to the transducer by placing the one end of the sleeve standard 10 onto shoulder 8. That end of standard 10 has a well defined distance from the reflector 10a in standard 10, while the front end of transducer 12, when inserted in holder 7, has a well defined distance from shoulder 8 as stated. Thus, the distance of transducer 12 from reflector 10a is well established for purposes of calibration.

The element 10 has openings so that the water can also enter the space between transducer 12 and the reflecting body 10a. The relative disposition of the reflector 10a to transducer 12 is independent from the angular adjustment of the assembly 6, 7; the standard 10 follows that inclination because it is mounted coaxial with the transducer and its holder 7.

The invention is not limited to the embodiments described above but all changes and modifications thereof not constituting departures from the spirit and scope of the invention are intended to be included.

We claim:

1. A device for mounting an ultrasonic test transducer in a water container being open at the top, comprising:
    gimbal support means for suspension of the container;
    a cover plate having an opening and mounted to the top of the container, said cover having particular means for engagement with a test object to obtain a particular relation position to that test object;
    a frame extending down from the plate, adjacent to the opening into the container;
    a tubular mount having a particular axis; and
    means for mounting the tubular mount to the frame and securing the mount thereto at a selective angle of the axis, the transducer being received by and mounted in the mount in particular relation to the axis, so that the orientation of the transducer is determined by the selected angle, and the transducer faces the opening in any position of adjustment.

2. A device as in claim 1, including a holder for the transducer being placed in such mount, said holder having a shoulder and means for connecting a sleeve to the holder in a position in which such a sleeve is seated on the shoulder.

3. A device as in claim 1 the means of said cover plate for engagement being a plurality of balls for rolling engagement with an object in relation to which the transducer has been oriented.

4. A device as in claim 1, said frame having two plates with arcuate slots for clamping the mount at the selected angle.

5. A device as in claim 1, said frame being constructed so that an axis of the transducer will intersect a particular point in different angular positions of the mount, said cover plate being provided with means for engaging an object to be tested so that said point is located on the surface of the object.

* * * * *